United States Patent
Xiao et al.

(10) Patent No.: US 10,653,896 B2
(45) Date of Patent: May 19, 2020

(54) RADIOTHERAPY APPARATUS INCORPORATING MULTI-SOURCE FOCUSING THERAPY AND CONFORMAL AND INTENSITY-MODULATED THERAPY

(71) Applicant: OUR NEW MEDICAL TECHNOLOGIES, Shenzhen (CN)

(72) Inventors: Shiqun Xiao, Xi'an (CN); Haifeng Liu, Xi'an (CN)

(73) Assignee: OUR NEW MEDICAL TECHNOLOGIES, Shenzhen (CN)

( * ) Notice: Subject to any disclaimer, the term of this patent is extended or adjusted under 35 U.S.C. 154(b) by 632 days.

(21) Appl. No.: 15/358,140

(22) PCT Filed: May 22, 2014

(86) PCT No.: PCT/CN2014/078091
§ 371 (c)(1),
(2) Date: Nov. 22, 2016

(87) PCT Pub. No.: WO2015/176265
PCT Pub. Date: Nov. 26, 2015

(65) Prior Publication Data
US 2017/0246480 A1   Aug. 31, 2017

(51) Int. Cl.
*A61N 5/10* (2006.01)
*G21K 5/04* (2006.01)
*G21K 1/02* (2006.01)
*G21K 1/04* (2006.01)

(52) U.S. Cl.
CPC ......... *A61N 5/1084* (2013.01); *A61N 5/1081* (2013.01); *G21K 1/025* (2013.01); *G21K 1/046* (2013.01); *G21K 5/04* (2013.01); *A61N 2005/1094* (2013.01)

(58) Field of Classification Search
CPC .... A61N 5/10; A61N 5/1028; A61N 15/1045; A61N 2005/1019; A61N 2005/1094
USPC ........................................................ 600/1–8
See application file for complete search history.

(56) References Cited

U.S. PATENT DOCUMENTS

2004/0264629 A1* 12/2004 Tang ...................... A61B 6/032
378/7
2012/0257710 A1* 10/2012 Funk .................... A61B 6/4488
378/9

\* cited by examiner

Primary Examiner — Samuel G Gilbert

(57) ABSTRACT

A radiotherapy apparatus incorporating multi-source focusing therapy and conformal and intensity-modulated therapy is disclosed. The radiotherapy apparatus includes a base, a movable couch, a gantry, at least one therapeutic head, and a counterweight. The therapeutic head includes a shielding part, a source carrier received in the shielding part, provided with a focusing radioactive source for focused therapy and a conformal radioactive source for conformal and intensity-modulated radiotherapy, a switch part configured for controlling on/off the source, a shielding door configured for controllably shielding the radiation beams of the radioactive sources; and a collimator assembly. By using this apparatus, accurate multi-source focused therapy and conformal therapy can be implemented in a single current Gamma Knife device.

13 Claims, 5 Drawing Sheets

RADIOTHERAPY APPARATUS INCORPORATING MULTI-SOURCE FOCUSING THERAPY AND CONFORMAL AND INTENSITY-MODULATED THERAPY

TECHNICAL FIELD

The disclosure relates to the technical field of large medical equipment, and more particularly to a radiotherapy apparatus incorporating multi-source focusing therapy and conformal and intensity-modulated therapy.

BACKGROUND

Radiation therapy is a common treatment for treating a tumor. Stereotaxic gamma-ray systemic therapy system (hereinafter referred to as Gamma Knife) is a radiation therapy equipment, and there are generally two kinds of radiotherapy approach in the process of gamma-ray therapy, one for stereotactic focused radiation therapy with multi-source and another for intensity-modulated radiation therapy. The stereotactic multi-source focused radiation therapy approach refers to emit gamma radiation beams across the body of a patient and focus to one focal point through the body, and a high energy treatment point can be formed by sound and heat energy conversion in the area of the focal point, for destroying the tumor. However, when the shape of the tumor is complicated, a conformal radiotherapy would be needed. The so-called conformal intensity-modulation therapy refers to employ a multi-leaf collimator, to make a shape of a radiation field plane for treatment similar to the shape of the tumor.

Currently, there is no stereotaxic gamma-ray systemic therapy device that can integrate the stereotactic multi-source focused radiation therapy method with the conformal and intensity-modulated radiation therapy method. In other words, a single current Gamma Knife device cannot implement both accurate multi-source focused therapy and conformal therapy. Therefore, it is impossible to provide different treatment options in the same device for different or same tumors.

SUMMARY

The present disclosure provides a radiotherapy apparatus incorporating multi-source focusing therapy and conformal and intensity-modulated therapy, to achieve a purpose of implementing both accurate multi-source focused therapy and conformal therapy in a single Gamma Knife device.

One embodiment of the present disclosure provides a radiotherapy apparatus incorporating multi-source focusing therapy and conformal and intensity-modulated therapy, comprising a base, a movable couch, a gantry, at least one therapeutic head, and a counterweight, the movable couch and the gantry are disposed on the base, the therapeutic head and the counterweight are oppositely positioned on the gantry. The therapeutic head comprises: a shielding part, configured for shielding radiation beams from at least one radioactive source; a source carrier received in the shielding part, provided with a focusing radioactive source for focused therapy and a conformal radioactive source for conformal and intensity-modulated radiotherapy; a switch part positioned on an emitting side of the focusing radioactive source and the conformal radioactive source, and comprises at least one through hole to be controlled aligning with the focusing radioactive source or the conformal radioactive source for passing through the radiation beams; a shielding door positioned on one side of the switch part away from the source carrier, configured for controllably shielding the radiation beams of the radioactive sources; and a collimator assembly, comprising a collimator carrier, and a plurality of focusing collimators and a multi-leaf collimator disposed on the collimator carrier.

Preferably, at least two rows of focusing radioactive sources are arranged on opposite sides of the source carrier, and a conformal radioactive source is disposed in the middle of the source carrier.

Preferably, each row comprises 9 focusing radioactive source for focused therapy and is equidistantly distributed in an arc sector with a central angle arranged between 26° to 60°, along an radial axial cross section of the gantry.

Preferably, the two rows of focusing radioactive sources are distributed on two sides of the conformal radioactive source with an included angle arranged between 26° to 60°, along an axial radial cross section of the gantry.

Preferably, the through hole comprises two rows of first through holes provided on two lateral lines of the switch part and corresponding to the focusing radioactive source for focused therapy, and a second through hole arranged in the middle of the switch part corresponding to the conformal radioactive source for conformal therapy, and the second through hole is offset from a symmetry line of the two rows of first through holes.

Preferably, the shielding door comprises two layers which are respectively movable in perpendicular directions to mutually be opened or closed.

Preferably, the focusing collimator is mounted on the collimator carrier and capable of moving together with the collimator carrier, and comprises three groups of collimating holes corresponding to the source carrier for directing the focusing radiation from the focusing radioactive sources, each group of collimating holes comprises two rows of collimating holes with same aperture diameter, and the distance between two rows of collimating holes in each group is substantially equal, and the apertures size of the collimating holes in different group are different.

Preferably, the focusing collimator is provided with a square hole in the middle of two rows of collimating holes of each group, and the multi-leaf collimator is received in the square hole.

The present invention further provides a collimator assembly comprising: a collimator carrier, and a plurality of focusing collimators and at least one multi-leaf collimator disposed on the collimator carrier. The focusing collimator is provided with a square hole and groups of collimating holes configured for directing the radiation emitted by corresponding radioactive sources, each group of collimating holes comprises two rows of collimating holes in same aperture diameter, and the apertures size of the collimating holes in different group are different, two rows of collimating holes in each group are located on two sides of the square hole with substantially same distance.

Preferably, the focusing collimators comprise three groups of collimating holes.

By using the radiotherapy apparatus incorporating multi-source focusing therapy and conformal and intensity-modulated therapy disclosed in the present invention, both accurate multi-source focused therapy and conformal therapy can be implemented in one radiotherapy apparatus.

DETAILED DESCRIPTION

For making the purpose, the technical proposal and advantages of embodiments of the disclosure more clear, the technical proposal of the embodiments of this disclosure may be described clearly and fully using the figures included. Clearly, the described embodiments are only parts of the embodiments of this disclosure and not all of the embodiments. Based on the embodiments of this disclosure, all other embodiments obtained without contributing any creative effect by those skilled in the art are within the scope of protection of this disclosure.

Figure 1:
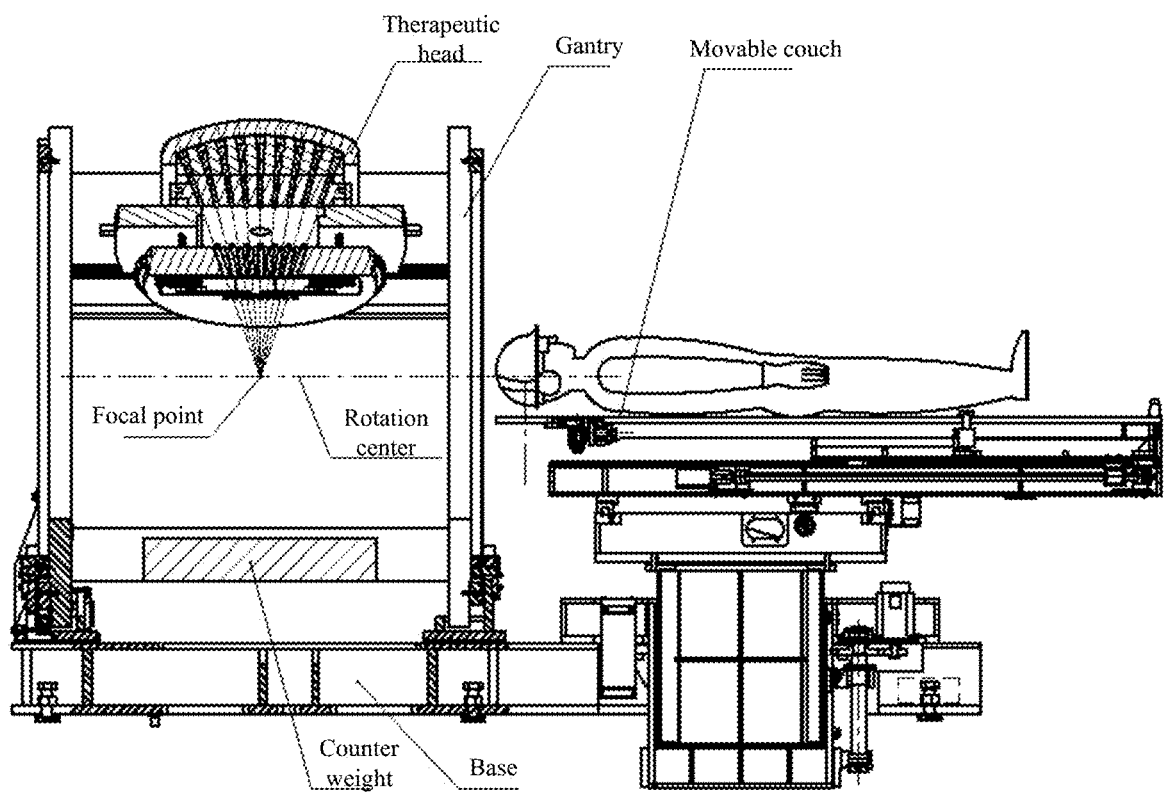
FIG. 1 is a schematic view of a radiotherapy apparatus incorporating multi-source focusing therapy and conformal intensity modulation therapy, according to an embodiment of the present disclosure.

In order to better understand the technical solution of the present invention, the Applicant has explained the radiation therapy system of the embodiment of the present invention by way of the specific embodiment of FIG. 1. FIG. 1 is a schematic view of a radiotherapy apparatus incorporating multi-source focusing therapy and conformal intensity modulation therapy, according to an embodiment of the present invention. As shown in FIG. 1, the radiotherapy apparatus includes a base, a gantry, a therapeutic head, a counterweight, and a movable couch. The base supports the whole radiotherapy apparatus, and plays a role of carrying the whole radiotherapy apparatus and a role of fixation. The gantry is arranged on the base, and is connected to the base by a rolling support. The gantry 40 rotates around an axial line by means of, e.g. gear driving, to achieve purpose of rotational treatment. The therapeutic head is the core component of the whole device, and is connected with the gantry. The therapeutic head is driven by the gantry to rotate around the gantry axis to perform rotational treatment. The therapeutic head may perform focused irradiation by focusing the radiation of cobalt source, or may perform conformal irradiation by passing radiation of a conformal cobalt source through a multi-leaf collimator. The counterweight is mounted on the gantry relative to the therapeutic head, for balancing the weight of the therapeutic head, so that the gravity center of the gantry coincides with its rotation center, to ensure the stability of the gantry in the process of rotation. The treatment couch is arranged on the base, and is movably connected to the base, e.g. by screws and/or pins. The treatment couch is used to support and position a patient, and can accurately deliver the patient to a specified position for treatment.

Figure 2:
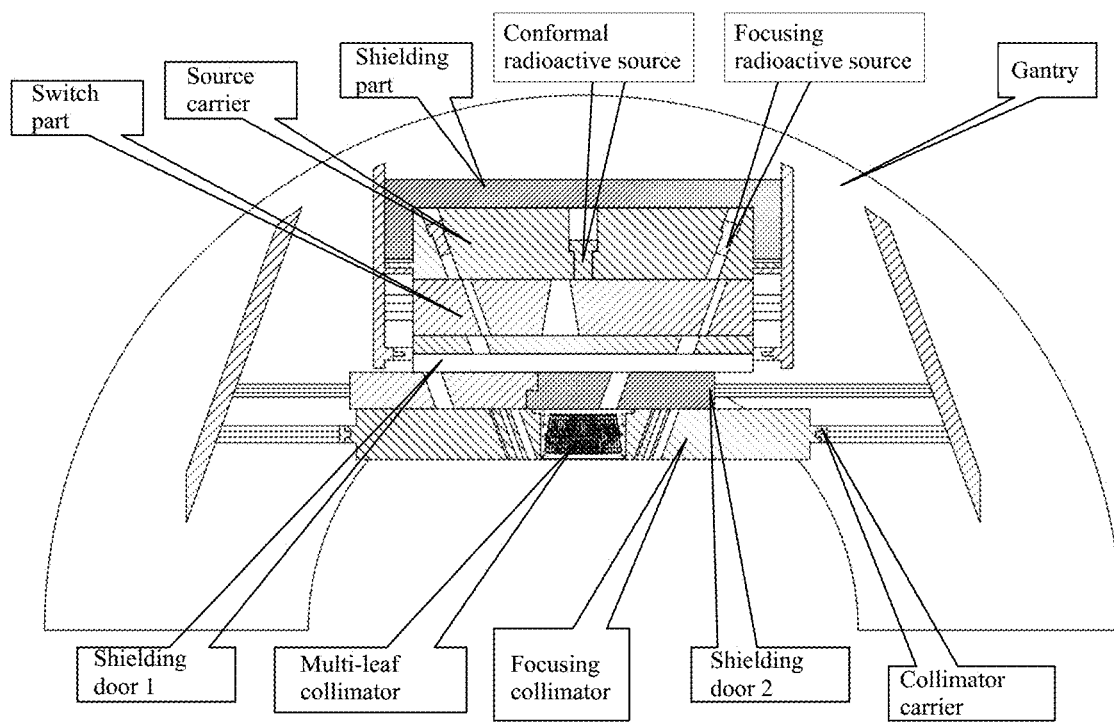
FIG. 2 is a schematic cross-sectional view of a therapeutic head of the radiotherapy apparatus of FIG. 1.
Figures 3A, 3B, 3C:
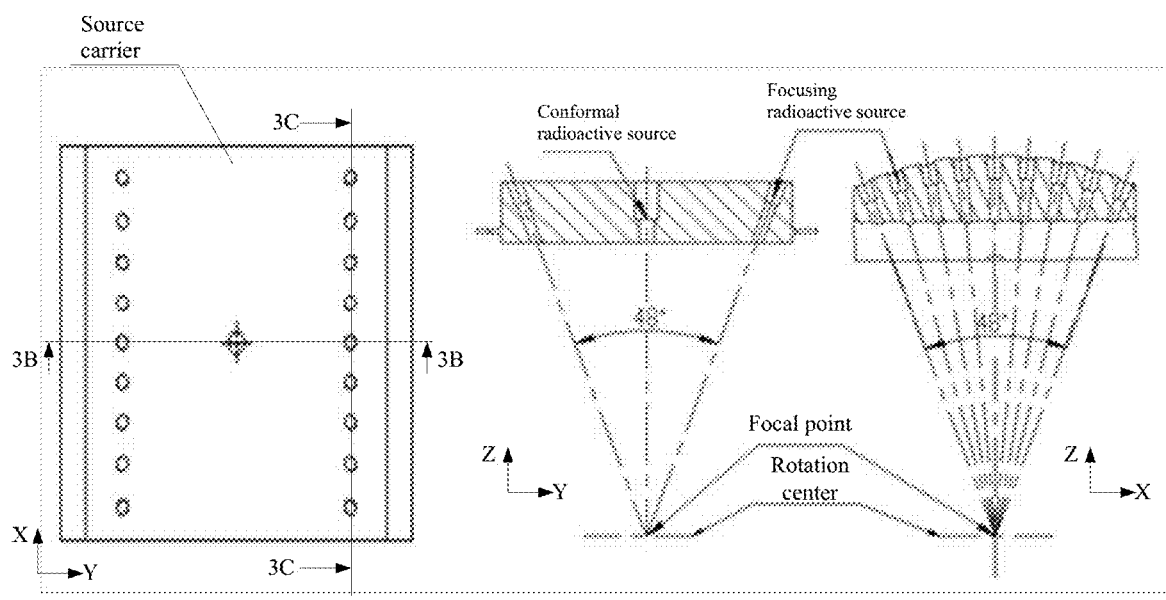
FIG. 3A is a schematic view from a top surface of a source carrier of the therapeutic head of FIG. 2.
FIG. 3B is a cross-sectional schematic view along line 3B-3B of the source carrier of FIG. 3A.
FIG. 3C is a cross-sectional schematic view along line 3C-3C of the source carrier of the therapeutic head of FIG. 2.

In combination of FIGS. 2 to 3B, the therapeutic head which is the core component of the overall device, comprises a shielding part, a source carrier, a switch part, a shielding door, a collimator carrier, a focusing collimator, a multi-leaf collimator, and associated drive or motivation support members which are not shown FIG. 2. The driving or motivation support members (hereinafter referred to as driving members) are conventional technology skilled in the art and will not be described in this embodiment as long as it can realize the functions mentioned below.

The shielding part is configured to isolate the radioactive source from the external environment, to shield the radiation of the radioactive source. The source carrier is located in the shielding part, and two rows of radioactive sources in total of 18 (for each row of 9) are arranged on the opposite sides of the source carrier for focusing therapy. The middle of the source carrier is also provided with a radioactive source for conformal therapy (hereafter referred to as conformal source), as shown in FIG. 3A. The conformal source is centered in the source carrier and the two rows of focusing sources have an included angle of 26° to 60° in the axial cross section (i.e., the plane parallel to the Z-Y plane in FIG. 2), preferably, the focusing sources are distributed on both sides with included angle of 48°, as shown in FIG. 3B. The source carrier are equidistantly distributed in an arc-shaped area from angle 26° to 60° in a radial cross section (i.e., a plane parallel to the Z-X plane in F FIG. 2, and X in F FIG. 2 is not shown, but it should be known that X is perpendicular to the Y-Z plane), as shown in FIG. 3C.

Figures 4A, 4B, 4C:
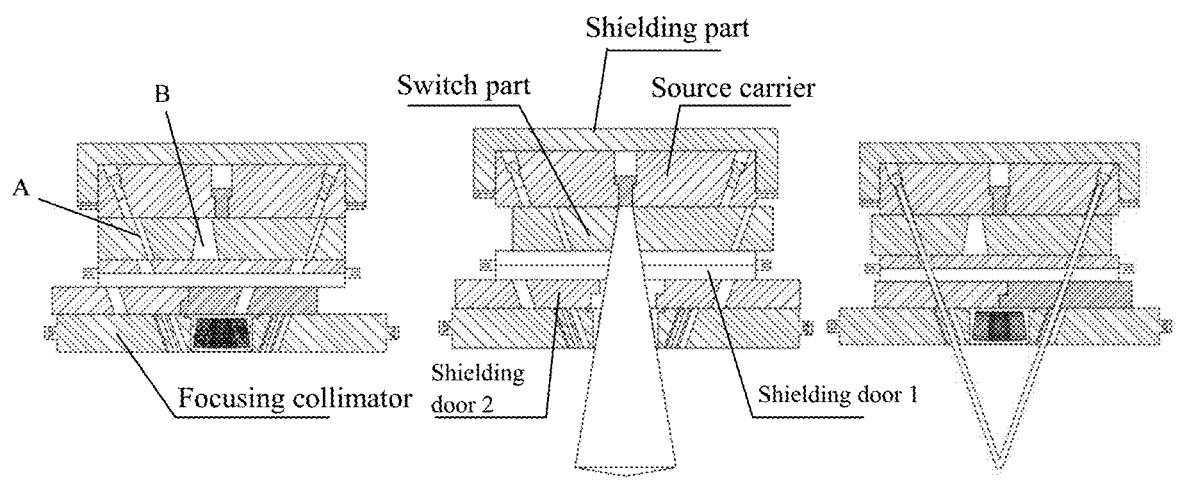
FIGS. 4A to 4C are the views of the position relation between the source carrier, switch part, shielding door, collimator carrier and collimator of the therapeutic head of FIG. 2, during two kinds of therapeutic sources being closed at the same time, and during the conformal source and the focused source being opened.

In combination of FIG. 2 and FIGS. 4A to 4B, the switch part is located on the side of the source carrier facing away from the shielding part, that is, under the source body, and the radiation emitted from the two radioactive sources is emitted from the same side. The switch part can move along the radial direction (i.e., in the Y-direction in FIG. 2) with respect to the source carrier driven by the driving members. Two sides of the switch part are provided with two rows of first through-holes A corresponding to the radioactive source for focusing therapy and a second through-hole B corresponding to the radioactive source for conformal therapy, and the second through-hole B is offset from the symmetrical line (not shown) of the two rows of first through-holes A. As such, the switch part is driven to three different positions corresponding to situations of simultaneously closing the two kinds of sources (FIG. 4A), opening the conformal source (FIG. 4B) and opening the focusing source (FIG. 4C).

In combination of FIG. 2, the shielding door is located on the side of the switch part facing away from the source carrier, configured for the purpose of controllably shielding the radiation of the radioactive source. The shielding door includes two layers respectively capable of being opened in radial direction and axial direction (i.e. the directions parallel to the direction of X and Y coordinates), thus the radiation can be completely shielded while the device is not on work. FIG. 2 only shows a second shielding door in a closed situation which is away from the switch part. Since the arrangement and the movement direction of a first shielding door closer to the switch part are perpendicular to that of the second shielding door, the state of the first shielding door is not shown in the schematic drawing, but the person skilled in the art will understand that the movement of the first shielding door coincides with that of the second shielding door.

Figure 5:
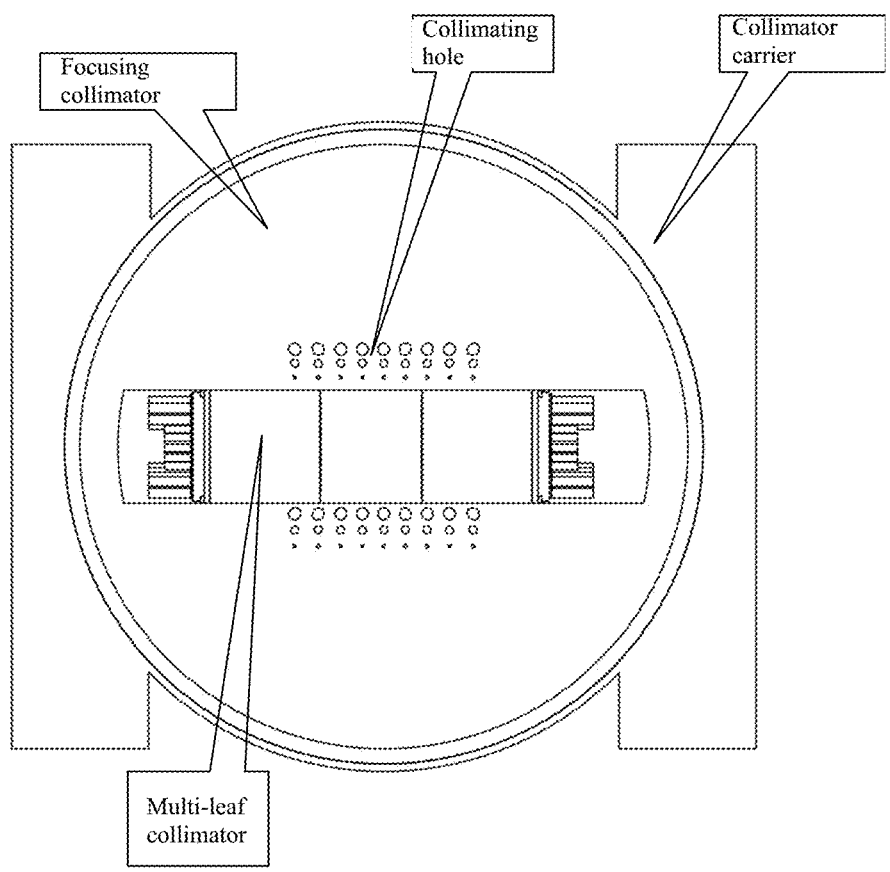
FIG. 5 is a schematic view of the collimator carrier of the therapeutic head of FIG. 2 with a focusing collimator and multi-leaf collimator disposed thereon.

Please refer to FIG. 2 and FIG. 5, the collimator carrier can be mounted inside the shielding door or outside the shielding door, and can rotate and move within the gantry. The collimator carrier is used for receiving the focusing collimators and the multi-leaf collimator so that the two kinds of collimators can be driven as required by the driving of the driving member. Thus, the collimator carrier, the focusing collimator and the multi-leaf collimator constitute a collimator combination. This arrangement can make the collimator and multi-leaf collimator placed on the same layer, saving a lot of space, so as to effectively increase the radial treatment space.

The focusing collimator is mounted on the collimator carrier and can be moved and rotated together therewith. The focusing collimator is provided with a square hole in the middle thereof. And three groups of collimating holes corresponding to the radioactive sources are arranged along two sides of the square hole, configured for collimating the focusing radiation. Each group of collimating holes includes two rows of collimating holes with same aperture diameter, and the aperture of the collimating holes in different groups is different. The distance between the two rows of collimating holes in each group is approximately equal. By choosing different collimating holes with different aperture, different sized focal points can be chosen, so that the focus is more accurate. Of course, the focusing collimator is not limited to three groups of collimating holes.

The multi-leaf collimator is mounted at the square hole of the focusing collimator. Different opening size with different shape is formed based on the movement of each blade of the multi-leaf collimator, to achieve a perfect match between the shape of the radioactive source and the shape of the tumor at the distance for therapy, to further achieve the conformal irradiation. The multi-leaf collimator would be prior art and will not be described again in this embodiment.

In the treatment of patients, at first, image acquisition for the patient is performed, and a treatment plan for the patient's lesions is made by a treatment planning software. At this time, the doctor will determine to choose which one of the focused head and the conformal head for treatment based on the shape, location, size of the tumor, or choose both of them to treat the lesion with one after another. After the plan is determined, it is sent to the control computer, and ready for treatment.

When the patient lies on the movable couch, the patient could be positioned thereon by means of a reset device and a fixation device. After the patient is positioned, a control machine for treatment reads the treatment plan of the patient to select one of the focused radiotherapy or the conformal radiotherapy. When the plan specifies employing the focused radiotherapy, the switch part is moved to an opening position of the focusing source, the two-layer shielding door are opened, the collimator carrier is moved to select the appropriate collimating hole according to the plan, to carry on the tumor treatment. When the plan specifies employing conformal therapy, the switch part is moved to an open position of the conformal source, the two-layer shielding door are opened, the multi-leaf collimator is also opened, and the radiation field corresponding to the plan is formed according to the planned position, to carry out tumor conformal treatment.

In the embodiment of the present invention, when the tumor of the patient is treated, a conformal irradiation, a focused irradiation, or a combination of the conformal irradiation and the focused irradiation can be selected according to the shape and size of the tumor, adapted to treat tumor in different shapes, to achieve a more perfect therapeutic effect.

It is to be understood that the foregoing is intended only as a specific embodiment of the disclosure and is not intended to limit the scope of the disclosure. The scope of protection of the present disclosure is to be understood to be within the scope of the present disclosure as defined by the equivalents thereof or equivalents thereof or to any other related art, either directly or indirectly, by the use of the present specification and drawings.

We claim:

1. A radiotherapy apparatus incorporating multi-source focusing therapy and conformal and intensity-modulated therapy, comprising a base, a movable couch, a gantry, at least one therapeutic head, and a counterweight, the movable couch and the gantry are disposed on the base, the therapeutic head and the counterweight are oppositely positioned on the gantry, wherein, the therapeutic head comprises:
   a shielding part configured for shielding radiation beams from at least one radioactive source;
   a source carrier received in the shielding part, provided with a focusing radioactive source for focused therapy and a conformal radioactive source for conformal and intensity-modulated radiotherapy;
   a switch part positioned on an emitting side of the focusing radioactive source and the conformal radioactive source, and wherein the switch part comprises at least one through hole to be aligned with the focusing radioactive source or the conformal radioactive source for passing through the radiation beams while the switch part is rotated to at least one predetermined position;
   a shielding door positioned on one side of the switch part away from the source carrier, configured for controllably shielding the radiation beams of the radioactive sources; and
   a collimator assembly comprising a collimator carrier, a plurality of focusing collimators and a multi-leaf collimator, wherein the focusing collimators and multi-leaf collimator are disposed on the collimator carrier.

2. The radiotherapy apparatus of claim 1, wherein at least two rows of focusing radioactive sources are arranged on opposite sides of the source carrier, and a conformal radioactive source is disposed in middle of the source carrier.

3. The radiotherapy apparatus of claim 2, wherein each said row comprises nine focusing radioactive source for focused therapy and is equidistantly distributed in an arc sector with a central angle arranged between 26° to 60°, along an axial cross section of the gantry.

4. The radiotherapy apparatus of claim 3, wherein the at least two rows of focusing radioactive sources are distributed on two sides of the conformal radioactive source with an included angle arranged between 26° to 60°, along an radial cross section of the gantry.

5. The radiotherapy apparatus of claim 4, wherein the at least one through hole comprises two rows of first through holes provided on two lateral lines of the switch part and corresponding to the focusing radioactive source for focused therapy, and a second through hole arranged in middle of the switch part corresponding to the conformal radioactive source for conformal therapy, and the second through hole is offset from a symmetry line of the two rows of first through holes.

6. The radiotherapy apparatus of claim 3, wherein the at least one through hole comprises two rows of first through holes provided on two lateral lines of the switch part and corresponding to the focusing radioactive source for focused therapy, and a second through hole arranged in middle of the switch part corresponding to the conformal radioactive source for conformal therapy, and the second through hole is offset from a symmetry line of the two rows of first through holes.

7. The radiotherapy apparatus of claim 1, wherein all of the focusing collimators are mounted on the collimator carrier and capable of moving together with the collimator carrier, and comprises three groups of collimating holes corresponding to the source carrier for directing the focusing radiation from the focusing radioactive sources, each said group of collimating holes comprises two rows of collimating holes with same aperture diameter, and distance between the two rows of collimating holes in each said group is equal, and the apertures size of the collimating holes in different group are different.

8. The radiotherapy apparatus of claim 7, wherein a square hole is disposed in middle of the said groups of collimating holes, and the multi-leaf collimator is received in the square hole.

9. The radiotherapy apparatus of claim 1, wherein the at least one through hole comprises two rows of first through holes provided on two lateral lines of the switch part and corresponding to the focusing radioactive source for focused therapy, and a second through hole arranged in middle of the switch part corresponding to the conformal radioactive source for conformal therapy, and the second through hole is offset from a symmetry line of the two rows of first through holes.

10. The radiotherapy apparatus of claim 1, wherein the shielding door comprises two layers which are respectively movable in perpendicular directions to mutually be opened or closed.

11. The radiotherapy apparatus of claim 1, wherein the at least one through hole comprises two rows of first through holes provided on two lateral lines of the switch part and corresponding to the focusing radioactive source for focused therapy, and a second through hole arranged in middle of the switch part corresponding to the conformal radioactive source for conformal therapy, and the second through hole is offset from a symmetry line of the two rows of first through holes.

12. A collimator assembly comprising: a collimator carrier, and a plurality of focusing collimators and at least one multi-leaf collimator disposed on the collimator carrier, wherein the focusing collimator is provided with a square hole and groups of collimating holes configured for directing the radiation emitted by corresponding radioactive sources, each said group of collimating holes comprises two rows of collimating holes in same aperture diameter, and the apertures size of the collimating holes in different group are different, distance between a center of the square hole to each of the two rows of collimating holes is the same.

13. The collimator assembly of claim 12, wherein the plurality of focusing collimators comprise three groups of collimating holes.

* * * * *